United States Patent
Pei et al.

(10) Patent No.: US 12,031,971 B2
(45) Date of Patent: Jul. 9, 2024

(54) METHOD FOR TESTING FROST SUSCEPTIBILITY OF SOILS AND ASSOCIATED APPARATUS

(71) Applicant: Northwest Institute of Eco-Environment and Resources, Chinese Academy of Sciences, Gansu (CN)

(72) Inventors: Wansheng Pei, Gansu (CN); Jiazuo Zhou, Gansu (CN); Mingyi Zhang, Gansu (CN); Zeliang Ye, Gansu (CN); Ruiqiang Bai, Gansu (CN)

(73) Assignee: NORTHWEST INSTITUTE OF ECO-ENVIRONMENT AND RESOURCES, CHINESE ACADEMY OF SCIENCES, Gansu (CN)

( * ) Notice: Subject to any disclaimer, the term of this patent is extended or adjusted under 35 U.S.C. 154(b) by 107 days.

(21) Appl. No.: 17/847,515

(22) Filed: Jun. 23, 2022

(65) Prior Publication Data
US 2023/0366868 A1 Nov. 16, 2023

(30) Foreign Application Priority Data
May 11, 2022 (CN) .......................... 202210510459.0

(51) Int. Cl.
*G01N 33/24* (2006.01)
*G01N 1/28* (2006.01)
(Continued)

(52) U.S. Cl.
CPC ............. *G01N 33/246* (2013.01); *G01N 1/42* (2013.01); *G01N 1/44* (2013.01); *G01N 25/04* (2013.01);
(Continued)

(58) Field of Classification Search
CPC ...... G01N 33/246; G01N 25/04; G01N 25/56; G01N 25/58; G01N 1/42; G01N 1/44; G01N 2001/2873
See application file for complete search history.

(56) References Cited

U.S. PATENT DOCUMENTS 3,447,615 A * 6/1969 Schick ..................... E21B 25/08
73/863.11
5,062,309 A * 11/1991 Voll .......................... G01N 1/08
73/864.44
(Continued)

FOREIGN PATENT DOCUMENTS

CN 103471884 A 12/2013
CN 104749205 A 7/2015
(Continued)

OTHER PUBLICATIONS

Zeinali, Amin et al., "Freezing-Thawing Laboratory Testing of Frost Susceptible Soils", Proceedings of the 17th Nordic Geotechnical Meeting, Challenges in Nordic Geotechnic May 28, 2016. (Year: 2016).*
(Continued)

*Primary Examiner* — Paul M. West
(74) *Attorney, Agent, or Firm* — Dority & Manning, P.A.

(57) ABSTRACT

The present disclosure provides a method for testing frost susceptibility of soils and an associated apparatus, and relates to the field of testing technology. The method includes: taking a part of a soil sample to be tested as test soil sample and freezing the test soil sample; taking a soil sample of outer layer from the test soil sample after the completion of freezing and measuring the moisture ratio of the soil sample of outer layer; and determining the frost susceptibility of the soil sample to be tested based on an initial moisture ratio and the moisture ratio of the soil sample of outer layer or based on the moisture ratio of the soil sample of outer layer and the moisture ratio of a soil sample of inner layer from the test soil sample after the completion of freezing, frost susceptibility.

17 Claims, 7 Drawing Sheets

(51) Int. Cl.
  *G01N 1/42* (2006.01)
  *G01N 1/44* (2006.01)
  *G01N 25/04* (2006.01)
  *G01N 25/56* (2006.01)
  *G01N 25/58* (2006.01)

(52) U.S. Cl.
  CPC .............. *G01N 25/56* (2013.01); *G01N 25/58* (2013.01); *G01N 2001/2873* (2013.01)

(56) References Cited

U.S. PATENT DOCUMENTS

| | | |
|---|---|---|
| 9,880,081 B1 | 1/2018 | Gupta |
| 2008/0202220 A1 | 8/2008 | Schmidt |

FOREIGN PATENT DOCUMENTS

| | | |
|---|---|---|
| CN | 204789419 U | 11/2015 |
| CN | 106613882 A | 5/2017 |
| CN | 107621476 A | 1/2018 |
| CN | 108181343 A | 6/2018 |
| CN | 109283208 A | 1/2019 |
| CN | 211478117 U | 9/2020 |
| CN | 112913488 A | 6/2021 |
| RU | 2585953 C1 * | 6/2016 |
| SU | 855462 A1 | 8/1981 |
| WO | WO2019214007 A1 | 11/2019 |

OTHER PUBLICATIONS

Chinese Office Action (w/ English translation) for corresponding Application No. 202210510459.0, dated Feb. 10, 2023, 11 pages.

* cited by examiner

Examples of soil samples excised by cutting rings

METHOD FOR TESTING FROST SUSCEPTIBILITY OF SOILS AND ASSOCIATED APPARATUS

CROSS-REFERENCE TO RELATED APPLICATION

The present disclosure claims the priority to the Chinese patent application with the filing No. 2022105104590 filed on May 11, 2022 with the Chinese Patent Office, and entitled "Method for Testing Soil Sample Freezing and Associated Apparatus", the contents of which are incorporated herein by reference in entirety.

TECHNICAL FIELD

The present disclosure relates to the field of testing technology, and particularly relates to a method for testing frost susceptibility of soils and an associated apparatus.

BACKGROUND

Figure 1:
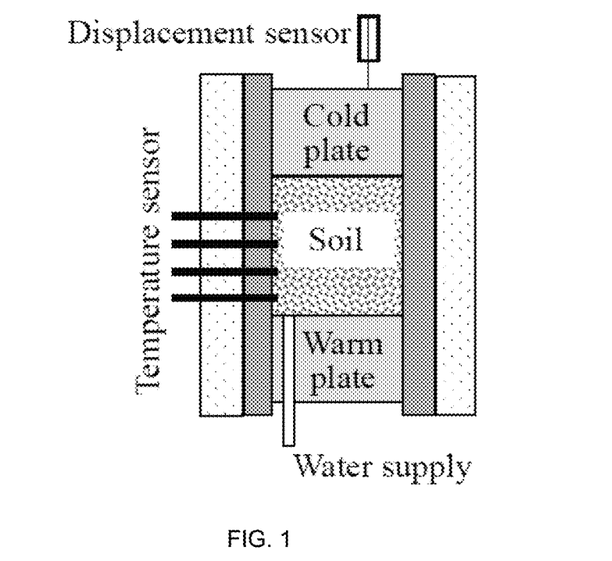
FIG. 1 is a structural schematic diagram of a device for one-dimensional soil column freezing test according to the prior art.
Figure 2:
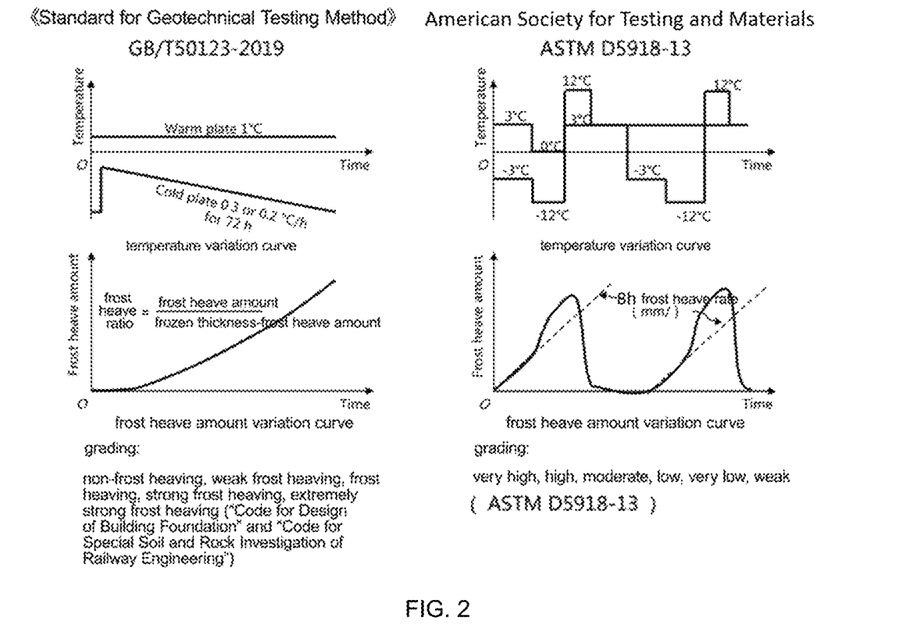
FIG. 2 is schematic diagrams showing changes in temperature and frost heave amount of a one-dimensional soil column freezing test according to the prior art.

At present, the frost susceptibility of a soil sample is determined in the engineering field mostly relying on a frost heave ratio of the soil sample measured in tests, or a maximum frost heave ratio, it is required to simulate the frost heave amount of the soil mass in the actual environment of a project, and the test cycle is relatively long. As testing method, a one-dimensional soil column freezing test is often employed, as shown in FIG. 1; as for the one-dimensional soil column freezing test, a sample having a diameter of 100 millimeters and a height of 100 millimeters is placed in an axially freezing device, the top of the sample is in contact with a cold plate, the bottom of the sample is in contact with a warm plate, and the circumference of the sample is wrapped by a heat insulating material so as to eliminate radial heat flux. During freezing, the temperature of the cold plate is set below the freezing point, the temperature of the warm plate is set above the freezing point, and the warm plate is in connection with a pipe for water supply. The cold plate of the device is stationary, while the warm plate is attached to a loading rod movable upwards and downwards. In a case of frost heave, the soil sample expands and pushes the warm plate downwards, hereby recording an axial displacement and calculating the frost heave ratio. This process further requires freezing according to the time and the temperature specified by the standard. As shown in FIG. 2, the temperature of the warm plate and the temperature of the cold plate are controlled at the same time, and the testing process takes a long time to obtain a better effect on frost heave amount.

Results for measurement of the frost susceptibility of soil samples through the one-dimensional soil column freezing test are intuitive and relatively accurate, but as far as the test itself is concerned, the analytical instruments are bulky, expensive, and relatively complicated to mount and use, which indicates the suitableness only for laboratory environments, and it is disadvantageous for practical engineering applications such as field study and design of roadbed and foundation, soil stability measurement, and stability of foundation or roadbed structures in cold region engineering. Thus, how to test a soil sample and accordingly determine the frost susceptibility with a low-cost and less time-consuming method has become a technical problem that needs to be solved.

SUMMARY

An object of the present disclosure is to provide a method for testing soil sample freezing and an associated apparatus, so as to solve technical problems in the prior art regarding high costs and time-consuming for determining the frost susceptibility of a soil sample.

To achieve the above-mentioned object, following technical solutions are employed in embodiments of the present disclosure.

In a first aspect, an embodiment of the present disclosure provides a method for testing frost susceptibility of soils, comprising steps of: taking a part of a soil sample to be tested as test soil sample and freezing the test soil sample; taking a soil sample of outer layer from the test soil sample after the completion of freezing and measuring the moisture ratio of the soil sample of outer layer; and determining the frost susceptibility of the soil sample to be tested based on an initial moisture ratio and the moisture ratio of the soil sample of outer layer or based on the moisture ratio of the soil sample of outer layer and the moisture ratio of a soil sample of inner layer from the test soil sample after the completion of freezing, wherein the moisture ratio of the soil sample of inner layer from the test soil sample after the completion of freezing is obtained by taking a soil sample of inner layer from the test soil sample after the completion of freezing and then measuring the moisture ratio of the soil sample of inner layer.

Optionally, the step of determining the frost susceptibility of the soil sample to be tested based on an initial moisture ratio and the moisture ratio of the soil sample of outer layer comprises a step of: determining the level of frost susceptibility of the soil sample to be tested according to a variation value in moisture ratio obtained by subtraction between the moisture ratio of the soil sample of outer layer and the initial moisture ratio and in accordance with a set range, in which the variation value in moisture ratio falls; and the step of determining the frost susceptibility of the soil sample to be tested based on the moisture ratio of the soil sample of outer layer and the moisture ratio of a soil sample of inner layer from the test soil sample after the completion of freezing comprises a step of: determining the level of frost susceptibility of the soil sample to be tested according to a moisture ratio difference obtained by subtraction between the moisture ratio of the soil sample of outer layer and the moisture ratio of the soil sample of inner layer from the test soil sample after the completion of freezing and in accordance with a set range, in which the moisture ratio difference falls.

Optionally, the method further comprises a step of obtaining an initial moisture ratio, the step comprising: taking a part of the soil sample to be tested as initially measured soil sample; and measuring the moisture ratio of the initially measured soil sample as initial moisture ratio.

Optionally, the method further comprises a step of obtaining an initial moisture ratio, the step comprising: using the remaining part after the removal of the soil sample of outer layer from the test soil sample after the completion of freezing as remaining soil sample; measuring the moisture content of the remaining soil sample; obtaining a total moisture content by adding the moisture content of the soil sample of outer layer and the moisture content of the remaining soil sample together; and obtaining a total moisture ratio as initial moisture ratio by dividing the total moisture content by a total mass before freezing the test soil sample or after the completion of freezing.

Optionally, the step of freezing the test soil sample comprises: performing heat insulating treatment for upper and lower surfaces of the test soil sample with a heat insulating material; and placing the test soil sample after the heat insulating treatment into a freezer for freezing.

Optionally, the test soil sample is a columnar soil sample excised by a cutting ring; and the step of taking a soil sample of outer layer from the test soil sample after the completion of freezing comprises: obtaining the soil sample of outer layer by cutting the surface of the test soil sample with a cutting ring.

Optionally, the moisture ratio is measured through following steps of: measuring a mass of moisture loss of the soil sample by drying as moisture content; and obtaining the moisture ratio according to the total mass of the soil sample and the measured moisture content.

Optionally, the soil sample to be tested is obtained in at least one of following manners: obtaining the soil sample to be tested by adding a set amount of water to a soil sample to be treated; obtaining the soil sample to be tested by performing heat and evaporation treatment on a soil sample to be treated; obtaining the soil sample to be tested by evaporating a set amount of water from a soil sample to be treated after immersed in water; and obtaining the soil sample to be tested by adding a set amount of water after the evaporation treatment of a soil sample to be treated.

In a second aspect, an embodiment of the present disclosure provides a soil sample freezing instrument, configured to freeze a test soil sample according to the first aspect, comprising: a heat insulation component; a cutting ring, of which an opening on one side is in detachable connection with the heat insulation component; a heat insulation cover, which is in detachable connection with an opening on the other side of the cutting ring, wherein the heat insulation cover is parallel to the bottom surface of the heat insulation component, when the opening on the one side of the cutting ring is in connection with the heat insulation component, while the opening on the other side is in connection with the heat insulation cover; and a refrigerator, enabling a refrigerating medium to flow in a space on the outer side of the cutting ring, which is located between the bottom surface of the heat insulation component and the heat insulation cover, wherein the freezing of the test soil sample is realized based on the flowing of the refrigerating medium, in a situation where the test soil sample is placed on the inner side of the cutting ring, which is located between the bottom surface of the heat insulation component and the heat insulation cover.

In a third aspect, an embodiment of the present disclosure provides an instrument for testing frost susceptibility of soils, configured to perform a freezing test on a test soil sample according to the first aspect, comprising: a box body; and a first cutting ring and a second cutting ring, wherein the diameter of the first cutting ring is greater than that of the second cutting ring, wherein the first cutting ring is used for accommodating the test soil sample; and the second cutting ring is used for excising a part of the radial periphery of the test soil sample as soil sample of outer layer; a freezer for freezing the test soil sample is fixed in the box body, the freezer includes a connecting structure detachable from the first cutting ring; the box body is provided therein with a heater for drying and removing moisture from the soil sample so as to measure a moisture content; and the box body is provided therein with an electronic scale for weighing the soil sample.

Optionally, the freezer further includes at least two heat insulation structures, which are respectively in detachable connection with the top surface and the bottom surface of the first cutting ring.

In a fourth aspect, an embodiment of the present disclosure provides an electronic apparatus, configured to carry out a method for testing frost susceptibility of soils according to the first aspect.

Compared with the prior art, the present disclosure has following beneficial effects.

As for the method for testing frost susceptibility of soils and the associated apparatus provided in embodiments of the present disclosure, the determination of the frost susceptibility can be realized by freezing a soil sample and measuring the distribution of a moisture ratio or a change in the moisture ratio, without the need to use a complex apparatus for one-dimensional soil column freezing tests according to the prior art. Thus, the technical solution of the present disclosure requires low costs, is less time-consuming, and meets requirements of projects on economic costs, time, and accuracy.

BRIEF DESCRIPTION OF DRAWINGS

In order to more clearly describe the technical solutions of the embodiments of the present disclosure, the drawings required to be used in the embodiments will be simply presented below; and it shall be understood that the following drawings merely show certain embodiments of the present disclosure, and thus should not be construed as limiting the scope thereof, and for a person ordinarily skilled in the art, further relevant drawings could be obtained according to these drawings without creative efforts.

DETAILED DESCRIPTION OF EMBODIMENTS

In order to make the objects, the technical solutions, and the advantages of the embodiments of the present disclosure clearer, the technical solutions in the embodiments of the present disclosure will be clearly and comprehensively described below with reference to the accompanying drawings in the embodiments of the present disclosure. Clearly, the described embodiments are merely some of the embodiments of the present disclosure, but not all the embodiments thereof. Generally, the assemblies of the embodiments of the present disclosure that are described and shown here in the accompanying drawings may be arranged and designed according to various configurations.

Thus, following detailed description of the embodiments of the present disclosure that are provided in the drawings merely represents selected embodiments of the present disclosure, rather than being intended to limit the scope of the present disclosure for which protection is sought. All other embodiments, which could be obtained by a person ordinarily skilled in the art on the basis of the embodiments in the present disclosure without creative efforts, shall fall within the scope of protection of the present disclosure.

In the description of the present disclosure, it should be clarified that relational terms such as first and second or the like are used merely for distinguishing one entity or operation from another entity or operation, and do not necessarily require or imply that there is any such practical relation or sequence between these entities or operations. Moreover, terms such as "comprise", "contain" or any other variants thereof are intended to encompass non-exclusive inclusion, such that a process, a method, an article, or an apparatus comprising a series of elements comprises not only those elements, but also comprises other elements that are not explicitly listed, or further comprises elements inherent in such a process, method, article, or apparatus. Without further limitations, an element defined by the phrase "comprising a . . . " does not exclude the presence of an additional identical element in a process, a method, an article, or an apparatus comprising the element.

Orientation or position relationships indicated by terms such as "upper", "lower" or the like are orientation or position relationships shown based on the accompanying drawings, or orientation or position relationships in which the product of this disclosure is conventionally placed during use, are used merely for the purpose of facilitating the description of the present disclosure and for simplifying the description, rather than indicating or implying that a specified device or element must be in a specific orientation, or be constructed and operated in a certain orientation, and therefore cannot be construed as limiting the present disclosure.

Terms such as "provide" and "connect" shall be construed in a broad sense. For example, it may be fixed connection, or detachable connection, or integrated connection; and it may be direct connection, or indirect connection via an intermediate medium, or inner communication between two elements. Regarding terms "soil sample" and "soil mass", a soil sample may also be construed as soil mass, and the terms "soil sample" and "soil mass" may be used interchangeably and both refer to an earth sample having a certain volume; alternatively, it could be understood in such a manner that a soil sample is a sample from a soil mass, the soil sample constitutes a part of the soil mass, and the soil sample can be deemed as representative of the soil mass, which means that tests on a soil sample are equivalent to tests on a soil mass. For a person ordinarily skilled in the art, the specific meanings of the above-mentioned terms in the present disclosure could be construed in accordance with specific circumstances.

Hereinafter, some embodiments of the present disclosure will be described in detail with reference to the accompanying drawings. The following embodiments and the features in the embodiments may be combined with each other without conflicts.

Existing results for measurement of frost susceptibility of soil samples are intuitive and relatively accurate, but there are still a series of shortcomings: the analytical instruments are bulky, expensive, and relatively complicated to mount and use, which indicates the suitableness only for laboratory environments; and the preparation of soil samples are difficult, the test periods last long, and one testing device can only proceed with one test, and the fault tolerance and the accuracy of tests are not high.

Figure 3:
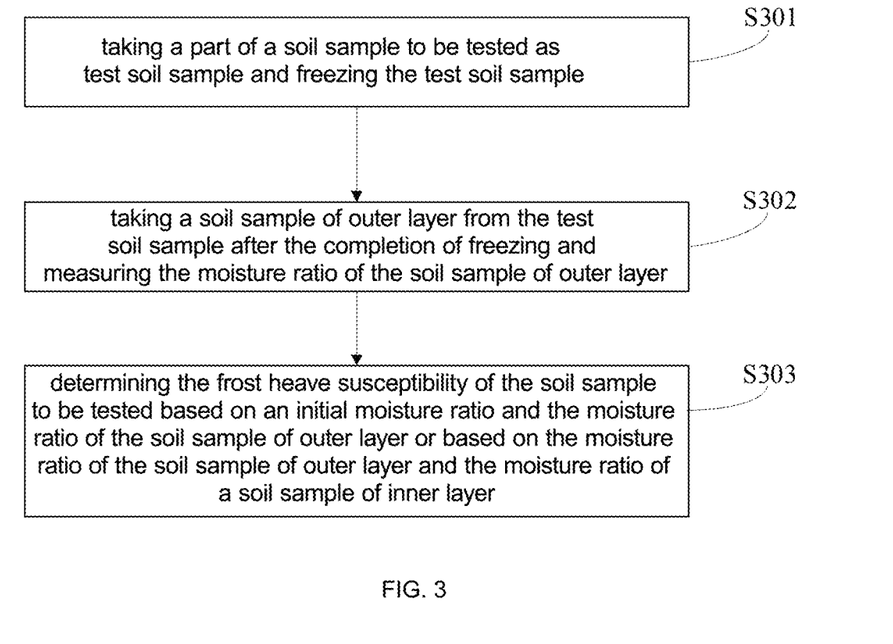
FIG. 3 is a flow chart of a method for testing frost susceptibility of soils according to an embodiment of the present disclosure.

In order to overcome above problems, referring to FIG. 3, an embodiment of the present disclosure provides a method for testing frost susceptibility of soils, comprising:

S301: taking a part of a soil sample to be tested as test soil sample and freezing the test soil sample;

S302: taking a soil sample of outer layer from the test soil sample after the completion of freezing and measuring the moisture ratio of the soil sample of outer layer; and S303: determining the frost susceptibility of the soil sample to be tested based on an initial moisture ratio and the moisture ratio of the soil sample of outer layer or based on the moisture ratio of the soil sample of outer layer and the moisture ratio of a soil sample of inner layer from the test soil sample after the completion of freezing.

In the above, the moisture ratio of the soil sample of inner layer from the test soil sample after the completion of freezing is obtained by taking a soil sample of inner layer from the test soil sample after the completion of freezing and then measuring the moisture ratio of the soil sample of inner layer.

Through the measurement and the analysis of changes in moisture ratio in foregoing steps, the determination of the frost susceptibility can be realized, without the need to use a complex apparatus for one-dimensional soil column freezing tests according to the prior art. Thus, the technical solution of the present embodiment requires low costs, is less time-consuming, and meets requirements of projects on economic costs, time, and accuracy. In addition, S303 can be performed only on the basis of the initial moisture ratio and the moisture ratio of the soil sample of outer layer, without the need to measure changes in the moisture ratio of an inner layer; alternatively, S303 can be performed only on the basis of the moisture ratio of the soil sample of outer layer and the moisture ratio of the soil sample of inner layer from the test soil sample after the completion of freezing, without the need to measure the initial moisture ratio, accordingly, the test steps are simplified maximally.

Figure 4:
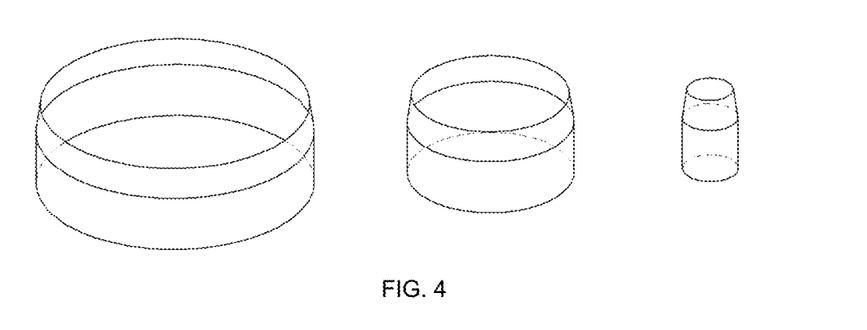
FIG. 4 is a schematic diagram showing a cutting ring according to an embodiment of the present disclosure.

In S301 and S302, in order to make the test results more accurate and easier to compare, the shapes of the test soil sample and the soil sample of outer layer can further be standardized, wherein the test soil sample may be cylindrical, or a flat cylinder, and it can be controlled such that both bottom surfaces of the cylinder are thermally insulated, and accordingly, the refrigeration is controlled to be conducted from the lateral surface of the cylinder towards the axial direction of the cylinder. In order to facilitate the preparation of a cylindrical soil sample, a cutting ring can be employed, and as shown in FIG. 4, the cutting ring is in a shortly tubular form, and a cylindrical soil sample can be obtained inside the cutting ring just by performing excision with the cutting ring. Hence, in an optional implementation, the test soil sample is a columnar soil sample excised by a cutting ring; and the step of taking a soil sample of outer layer from the test soil sample after the completion of freezing comprises: obtaining the soil sample of outer layer by cutting an outer layer of the test soil sample with a cutting ring. Accordingly, a desired soil sample can be obtained by utilizing the cutting ring method, the test soil sample is cylindrical, and the soil sample of outer layer may be tubular, wherein the forms thereof are regular, the tool is simple and easy to operate, and the preparation is easy to realize and saves both time and labor.

Figure 5:
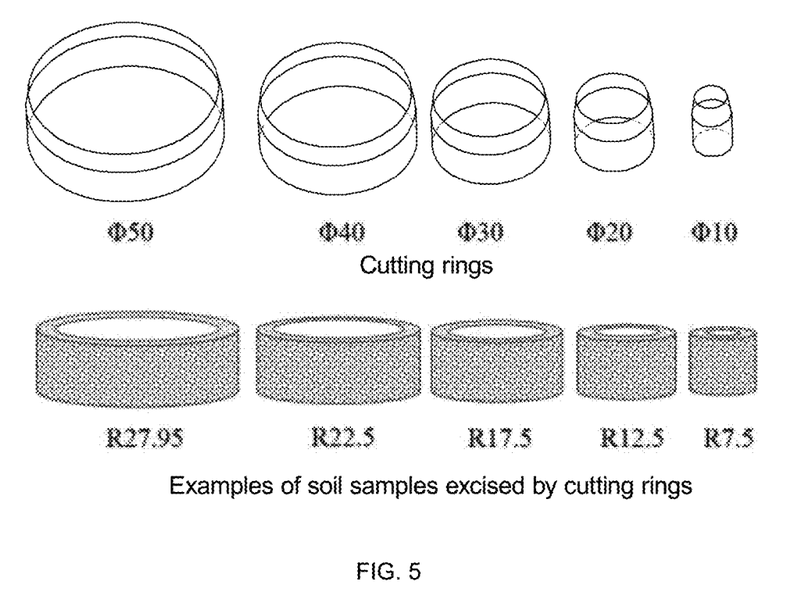
FIG. 5 is a schematic diagram showing some soil samples excised by the cutting ring according to an embodiment of the present disclosure.

It is further discovered by the applicant that a good test effect can be achieved by selecting a cutting ring with a proper size among cutting rings of numerous sizes, wherein an overlarge test soil sample is inconducive to a more significant change in moisture ratios of the inner layer and the outer layer, but a too small test soil sample would easily render relatively great error, meanwhile, an overlarge test soil sample results in difficulties regarding collection. Thus, in an optional implementation, regarding the dimensional range, the diameter of the cutting ring ranges from 40 mm to 65 mm. As shown in FIG. 5, in an optional implementation, different annular or tubular soil samples can be excised as foregoing soil sample of inner layer or soil sample of outer layer, or rather hollow cylindrical soil samples and cylindrical soil samples, for example, R22.5-R25 is used as soil sample of outer layer, and R7.5-R10 is used as soil sample of inner layer, or a cylindrical soil sample within R5 can be used as soil sample of inner layer, and various feasible sizes and combinations can be formed. Moisture ratios of excised soil samples of all layers may also be measured, and on the basis of the moisture ratios of soil samples of all the layers, e.g., on the basis of the maximum value of the difference values therebetween or the average of the moisture ratio differences of soil samples of respectively adjacent layers, the susceptibility of the soil sample to be tested to water migration can be determined, and the frost susceptibility of the soil sample to be tested can be determined accordingly.

In an optional implementation, the test soil sample is a saturated soil sample prepared by using a cutting ring, which is a cutting ring having a diameter of 61.8 mm and a height of 20 mm. Further, a cutting ring of r=28.0 mm can be used for cutting the surface of the test soil sample so as to obtain a soil sample of outer layer.

In order to make the test results more accurate and easier to compare, the process of S301 for freezing the test soil sample can be standardized. In an optional implementation, the step of freezing the test soil sample comprises: performing heat insulating treatment for upper and lower surfaces of the test soil sample with a heat insulating material; and placing the test soil sample after the heat insulating treatment into a freezer for freezing the same. Therefore, the internal freezing of the test soil sample can be divided into two directions, wherein the upward and downward directions are thermally insulated, and the refrigeration is conducted from the other directions, accordingly, it is unnecessary to give consideration to water migration in the upward and downward directions and to changes in moisture ratio in the upward and downward directions, which means that the measurement of test data is simplified. When the test soil sample is a cylinder, it can be controlled such that both bottom surfaces of the cylinder are thermally insulated, and accordingly, the refrigeration can be controlled to be conducted from the lateral surface of the cylinder towards the axial direction of the cylinder, which indicates radial freezing, and in this case, the frost susceptibility test of soils is a radial freezing test.

In respect of the selection of above heat insulating materials, EPS foam material can be selected. Hence, in an optional implementation, heat insulating treatment is performed on the upper and lower surfaces of the test soil sample with the EPS foam material, so as to eliminate the heat flux in the vertical direction. EPS foam represents a low-cost, convenient and efficient heat insulation manner.

By standardizing the process of S301 for freezing the test soil sample, the temperature and the duration of freezing can further be defined, for example, the step of freezing the test soil sample is performed in a thermostatic freezer, the temperature is adjusted to range from −5° C. to −20° C., and the duration of freezing is not less than 6 h. In an optional implementation, the freezing temperature is set as a constant temperature of −20° C., and the freezing lasts for 6 hours. In this way, it can be ensured that the test soil sample is thoroughly frozen and the distribution of water in the soil sample is immobilized.

Figure 6:
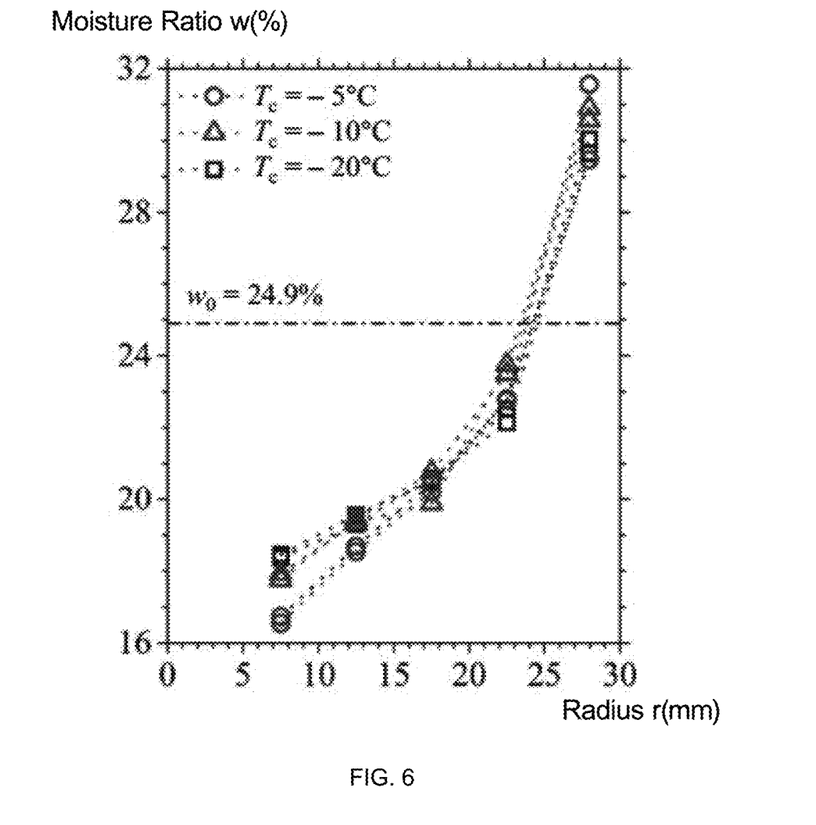
FIG. 6 is a comparison diagram showing freezing test results of the same soil sample at different temperatures according to an embodiment of the present disclosure.

Further, it is discovered by the applicant through experiments that whether the freezing temperature is high or low has relatively little influence on the determination of the frost susceptibility of the soil sample to be tested, that is to say, the determination result for the frost susceptibility of the soil sample to be tested is insusceptible to the freezing temperature. Before freezing, the test soil sample has a uniform and equal moisture ratio distribution, the ambient temperature during the freezing process is set to be −5° C., −10° C., and −20° C., and soil samples at respective positions are excised by utilizing a cutting ring similar to that in FIG. 5. After freezing, the experimental results are shown in FIG. 6, the water distribution situation of the test soil samples obtained at respective temperatures are consistent, and the differences in values and trends are small, indicating that whether the freezing temperature is high or low has no influence on the test results of this method, thus, the test restrictions are relaxed to a great extent. Thus, the test soil sample can be frozen faster at a lower temperature.

A person killed in the art would usually have no other effective freezing methods due to expenditure control or resource constraints; in this regard, it is further proposed in the present disclosure that with sufficient budget or under tight time requirements, a low-temperature environment with a special medium such as liquid nitrogen is used to freeze the sample for quick freezing, and multiple samples can be frozen simultaneously. In the step of freezing the test soil sample, dry ice, liquid nitrogen or the like may be used for refrigeration, and dry ice, liquid nitrogen or the like may be used for refrigerating the air and accordingly for refrigerating the test soil sample. Dry ice and an organic solvent such as ethanol can be mixed for refrigeration, and a sustained and stable low temperature effect can be achieved quickly. Generally, a small amount of ethanol is needed, and excessive dry ice is required; and the amount of ethanol can be appropriately increased according to the specific low temperature range.

For the whole embodiment, the change in moisture content is correlated with the moisture ratio of respective states such as the initial moisture ratio, and the correlation with the initial moisture ratio is relatively higher. Thus, the moisture content under certain natural conditions can be collected, e.g., selected season, selected soil samples of certain weather such as soil samples after rain; and manual intervention regarding the moisture content can also be performed on soil samples. Hence, in an optional implementation, the soil sample to be tested is obtained in at least one of following manners: obtaining the soil sample to be tested by adding a set amount of water to a soil sample to be treated; obtaining the soil sample to be tested by performing heat and evaporation treatment on a soil sample to be treated; obtaining the soil sample to be tested by evaporating a set amount of water from a water-immersed soil sample to be treated; and obtaining the soil sample to be tested by adding a set amount of water after the evaporation treatment of a soil sample to be treated. In this way, standardized treatment can be realized regarding the moisture ratio of the test soil sample so as to obtain a moisture ratio close to the expectation, or obtain a greater initial moisture ratio, which facilitates the observation of changes in moisture ratio.

In an optional implementation, the method further comprises a step of obtaining an initial moisture ratio, which step comprising: taking a part of the soil sample to be tested as initially measured soil sample; and measuring the moisture ratio of the initially measured soil sample as initial moisture ratio.

Compared with an initial moisture ratio speculated based on experiences or historical data, obtaining an initial moisture ratio from the initially measured soil sample represents a reliable way to obtain an initial moisture ratio.

The initial moisture ratio may also be obtained by using another optional implementation, for example, by using the remaining part after the removal of the soil sample of outer layer from the test soil sample after the completion of freezing as remaining soil sample; measuring the moisture content of the remaining soil sample; obtaining a total moisture content by adding the moisture content of the soil sample of outer layer and the moisture content of the remaining soil sample together; and obtaining a total moisture ratio as initial moisture ratio by dividing the total moisture content by a total mass of the test soil sample before freezing or after the completion of freezing. In this way, there is no need to measure a moisture ratio before freezing, on the contrary, it is only required to measure a moisture ratio after freezing, which is a way of simplifying test steps.

The moisture ratios in S302 and S303 can be obtained through the moisture content and the mass, and the moisture content can be measured in various ways. For example, to measure the moisture content of a soil sample, it is possible to make the soil sample undergo sufficient evaporation, and the reduction in the weight thereof due to evaporation is measured as moisture content. Evaporation can be realized by heating, lowering the air pressure or vacuumizing such that evaporation of moisture is accelerated. Hence, in an optional implementation, the step of measuring a moisture ratio comprises: measuring a mass of moisture loss of the soil sample after drying as moisture content; and obtaining the moisture ratio according to the total mass of the soil sample and the measured moisture content. The moisture content can be obtained quickly through drying. In an optional implementation, the step of measuring a moisture ratio comprises: placing the soil sample into a low-pressure environment or vacuumizing the same, such that the moisture runs off due to accelerated evaporation, or blowing dry gas onto the soil sample, or blowing hot dry gas onto the soil sample, and measuring a mass of moisture loss of the soil sample as moisture content; and obtaining the moisture ratio according to the total mass of the soil sample and the moisture content.

The moisture ratio or moisture content measured by the above way is simple and accurate, which helps to improve the overall efficiency for testing the test soil sample.

In an optional implementation, S303 comprises: firstly determining the susceptibility of the soil sample to be tested to water migration and accordingly determining the frost susceptibility of the soil sample to be tested based on the initial moisture ratio and the moisture ratio of the soil sample of outer layer or based on the moisture ratio of the soil sample of outer layer and the moisture ratio of the soil sample of inner layer from the test soil sample after the completion of freezing.

A more accurate and clearer initial judgment of the soil sample to be tested is obtained by firstly determining the susceptibility of the soil sample to be tested to water migration, which helps to further determine the frost susceptibility of the soil sample to be tested more accurately.

In an optional implementation, the step of determining the frost susceptibility of the soil sample to be tested based on an initial moisture ratio and the moisture ratio of the soil sample of outer layer in S303 comprises: determining the level of frost susceptibility of the soil sample to be tested according a variation value in moisture ratio obtained by subtraction between the moisture ratio of the soil sample of outer layer and the initial moisture ratio and in accordance with a set range, in which the variation value in moisture ratio falls. For example, the level of frost susceptibility of the soil sample to be tested is determined as weak, if the moisture ratio difference ranges from 0 to 0.3%.

Alternatively, in another optional implementation, the step of determining the frost susceptibility of the soil sample to be tested based on the moisture ratio of the soil sample of outer layer and the moisture ratio of a soil sample of inner layer from the test soil sample after the completion of freezing in S303 comprises: determining the level of frost susceptibility of the soil sample to be tested according to a moisture ratio difference obtained by subtraction between the moisture ratio of the soil sample of outer layer and the moisture ratio of the soil sample of inner layer from the test soil sample after the completion of freezing and in accordance with a set range, in which the moisture ratio difference falls.

With the set range, in which the moisture ratio difference falls, as a medium, the level of frost susceptibility of the soil sample to be tested can be determined simply and effectively.

In an optional implementation, the above moisture ratios obtained in S303 comprise one or more initial moisture ratios and moisture ratios of soil samples of outer layer, or comprise one or more moisture ratios of soil samples of outer layer and moisture ratios of soil samples of inner layer from the test soil sample after the completion of freezing; and the value of the susceptibility of a soil sample to be tested to water migration is obtained through functional operation, and the frost susceptibility of the soil sample to be tested can then be determined according to the value of the susceptibility to water migration. This function can determine the level of frost susceptibility of the soil sample to be tested based on a set range, in which the maximum value of the difference values between moisture ratios of soil samples of respective layers or the average of the moisture ratio differences of soil samples of respectively adjacent layers fall.

Through the functional operation, the data about moisture ratios can be comprehensively processed so as to reduce the error regarding the determination of the frost susceptibility of the soil sample to be tested.

Based on foregoing embodiments, an embodiment of the present disclosure further provides a soil sample freezing instrument, which can accordingly be used in a method provided in any embodiment of the present disclosure for freezing a test soil sample according to any one of foregoing embodiments, comprising: a heat insulation component; a cutting ring, of which an opening on one side is in detachable connection with the heat insulation component; a heat insulation cover, which is in detachable connection with an opening on the other side of the cutting ring, wherein the heat insulation cover is parallel to the bottom surface of the heat insulation component, when the opening on the one side of the cutting ring is in connection with the heat insulation component, while the opening of the other side is in connection with the heat insulation cover; and a refrigerator, enabling a refrigerating medium to flow in a space on the outer side of the cutting ring, which is located between the bottom surface of the heat insulation component and the heat insulation cover, wherein the freezing of the test soil sample is realized based on the flowing of the refrigerating medium, in a situation where the test soil sample is placed on the inner side of the cutting ring, which is located between the bottom surface of the heat insulation component and the heat insulation cover. The soil sample freezing instrument provided in the present embodiment has a simple structure, requires low costs, is able to prepare a soil sample quickly, and makes an efficient freezing process.

Figure 7:
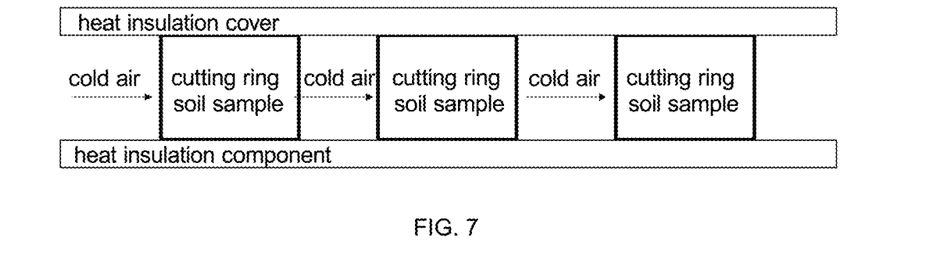
FIG. 7 is a structural schematic diagram of a soil sample freezing instrument according to an embodiment of the present disclosure.

In an optional implementation, there are multiple cutting rings, and each cutting ring can have individual heat insulation component and heat insulation cover, or multiple cutting rings can share one set of heat insulation component and heat insulation cover, as shown in the lateral view in FIG. 7. By using multiple cutting rings and sharing one set of heat insulation component and heat insulation cover for freezing a plurality of soil samples, a series of shortcomings of the testing method for one-dimensional soil column freezing tests according to the prior art are overcome: difficulties in the soil sample preparation of the testing method for one-dimensional soil column freezing tests, relatively long test period, and only one test allowed to be proceeded in one testing device, which reduces the fault tolerance of the test. Multiple test soil samples are prepared by the multiple cutting rings, and they are tested simultaneously, thus, the process is simple and costs shorter time.

Figure 8:
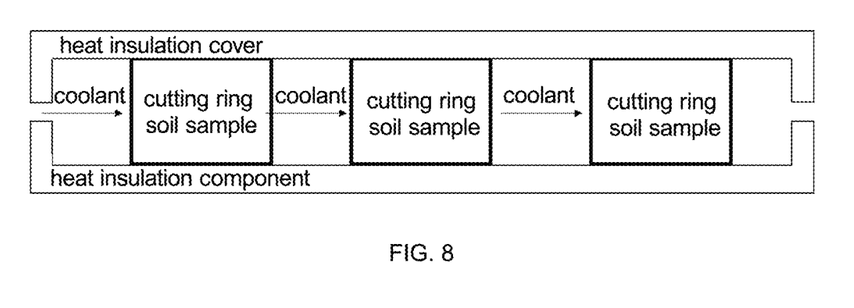
FIG. 8 is a structural schematic diagram of another soil sample freezing instrument according to an embodiment of the present disclosure.

In an optional implementation, the heat insulation component and the heat insulation cover have structures that are in mutually cooperative and connection, and the heat insulation component and the heat insulation cover can further form an integral box body having a port, and the refrigerator enables the refrigerating medium to enter through the port of the box body. FIG. 8 shows an example, wherein the refrigerating medium may be cold air. Dry ice, liquid nitrogen or the like may be used for refrigerating the air and accordingly for refrigerating the test soil sample.

An embodiment of the present disclosure further provides an instrument for testing frost susceptibility of soils, which is accordingly used in a method provided in any embodiment of the present disclosure for performing a freezing test on a test soil sample according to any one of foregoing embodiments, comprising: a box body; and a first cutting ring and a second cutting ring, wherein the diameter of the first cutting ring is greater than that of the second cutting ring, wherein the first cutting ring is used for accommodating the test soil sample; and the second cutting ring is used for excising a part of the radial periphery of the test soil sample as soil sample of outer layer; a freezer for freezing the test soil sample is fixed in the box body, the freezer includes a connecting structure detachable from the first cutting ring; the box body is provided with a heater for drying and removing moisture from the soil sample so as to measure a moisture content; and the box body is provided with an electronic scale for weighing the soil sample. A set of instrument for testing frost susceptibility of soils formed in this way can be integrated in a box body, which is convenient for researchers to carry and conduct rapid field tests on the spot.

In order to guarantee that the instrument for testing frost susceptibility of soils controls the heat flow direction of the soil frost susceptibility test, in an optional implementation, the freezer further includes at least two heat insulation structures, which are respectively in detachable connection with the top surface and the bottom surface of the first cutting ring. Therefore, it can be controlled such that during freezing, heat is transferred along the radial direction of the cylindrical soil sample in the cutting ring.

An embodiment of the present disclosure further provides an electronic apparatus or a computer storage medium, configured to carry out a method for testing frost susceptibility of soils as described above. The technical effect lies in further saving of manual labor and computational expense.

The applicant has studied the principle of the technical solution of the present disclosure: the on-site cause for frost heave of the soil mass is that free water in the soil is frozen into ice crystals, when the temperature of a soil layer reaches the freezing point. Along with the proceeding of freezing, loosely bound water begins to freeze, and the thickness of a bound water film becomes thinner, resulting in an increase in ion concentration, hereby enhancing the osmotic pressure and prompting the loosely bound water in an unfrozen area to migrate towards a frozen area, and then re-freeze and re-migrate. Such a vicious circle leads to continuous expansion of ice crystals and the soil mass is damaged due to frost heave. Water migration is the main cause of frost heave of the soil mass, so there is a strong correlation between the susceptibility of the soil mass to moisture migration and the frost susceptibility. A moisture content distribution curve obtained through experiments is shown in FIG. 6, illustrating the characteristic of gradual moisture migration from an unfrozen area to a frozen area during the freezing process. It is discovered through experiments that as for different soil masses, changes in water inhomogeneity after freezing and the data form of the maximum frost heave ratio are consistent. Therefore, it is feasible to determine the frost susceptibility from the susceptibility of soil mass to moisture migration.

In an embodiment with a better effect, three kinds of soils, i.e., silt, clay, and sand, were tested, and the salinity and the initial moisture ratio thereof were controlled and measured. A cutting ring specimen having a diameter of 61.8 mm and a height of 20 mm was prepared for use as test soil sample, referred to as specimen. Heat insulating treatment was performed on the upper and lower surfaces of the specimen with EPS foam material, and the openings of the cutting ring on both sides can be covered with the EPS foam material, so as to eliminate the heat flux in the vertical direction. Then, the treated specimen was placed in a cooler for freezing. The temperature was set to be −20° C. After about 6 hours, the specimen was thoroughly frozen, specimens of multiple layers were obtained by cutting the specimen with the cutting ring, and the moisture content distribution along the radial direction was then obtained by the drying method.

The moisture content difference $\Delta\omega_{o1}$ between the outermost layer and the innermost layer serves as an index parameter of water inhomogeneity or as a parameter characterizing water migration. The increase in moisture content of the outermost layer with respect to the initial moisture content, i.e., the variation value in moisture ratio, serves as a parameter characterizing water migration or as an index parameter of water inhomogeneity, denoted as $\Delta\omega_{o0}$. Compared with the need to cut the specimen layer by layer to obtain the innermost layer so as to acquire $\Delta\omega_{o1}$, it is only required to cut the outermost layer of the specimen once so as to acquire $\Delta\omega_{oO}$, which can save a lot of time in large-scale projects.

Figure 9:
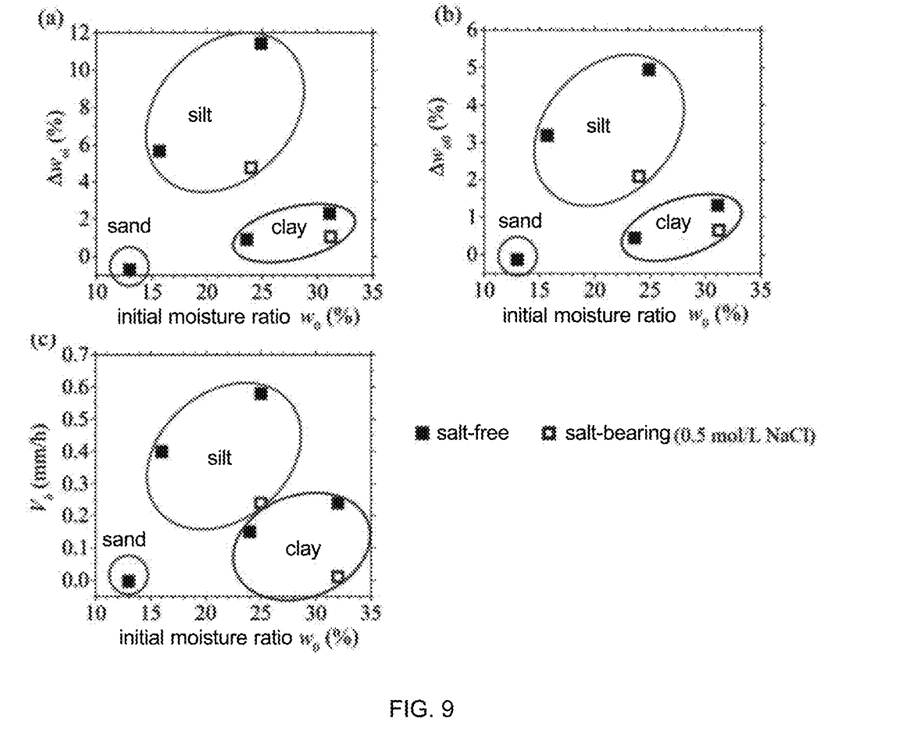
FIG. 9 is a comparison diagram showing test results for $\Delta\omega_{o1}$, $\Delta\omega_{oo}$ and Vh of clay, silt, and sand under different initial moisture contents and different salinity conditions according to an embodiment of the present disclosure.

After the test, the measured $\Delta\omega_{o1}$ of different soil samples is shown in FIG. 9(a), $\Delta\omega_{oO}$ is shown in FIG. 9(b), and the directly measured frost heave ratio $V_k$ is shown in FIG. 9(c). It should be noted that the longitudinal axis is different, while the horizontal axis is identical, and different specimens are compared in respect of $\Delta\omega_{o1}$ and $\Delta\omega_{oO}$. Although the value of $\Delta\omega_{o1}$ is roughly twice that of $\Delta\omega_{oO}$, the image morphological characteristics of the two are roughly the same, and they are also consistent with each other in the frost heave ratio. In contrast, $\Delta\omega_{oO}$ is much easier to acquire than $\Delta\omega_{o1}$ and is also easier to measure. Therefore, $\Delta\omega_{oO}$ can be used as an index of water inhomogeneity for evaluating soil mass frost heave.

It is further discovered by the applicant that the method according to the present disclosure achieves a higher precision for soil samples having a relatively small soil grain size, such as silt, so, in an optional implementation, can only be applied to tests of test soil samples having a relatively small soil grain size or silt soil samples, for example, a test soil sample having a maximum soil grain size less than 0.1 mm can be selected, or a test soil sample having a maximum soil grain size less than 0.2 mm can be selected, so as to implement the limiting of the existing test method for soil frost susceptibility.

Figure 10:
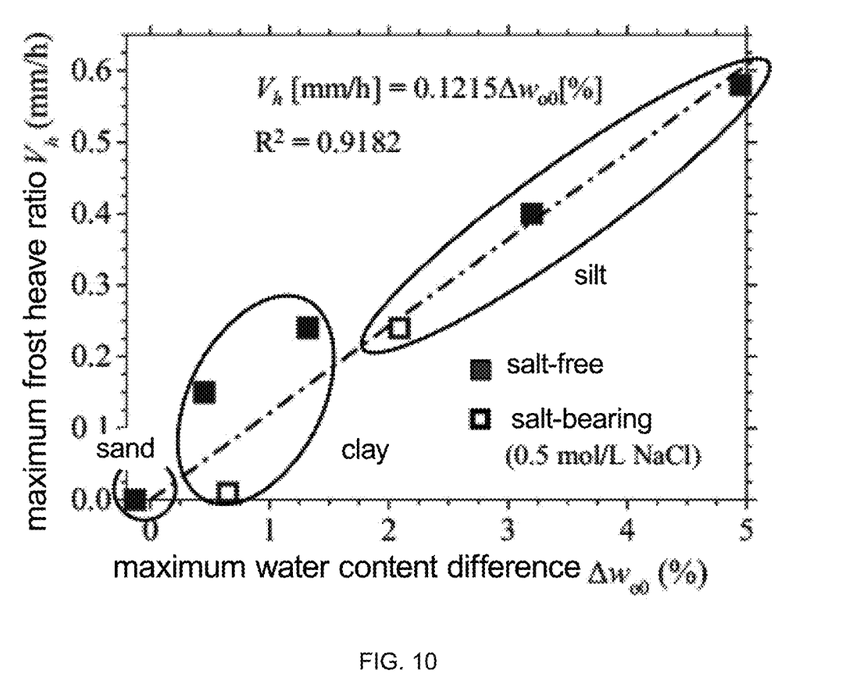
FIG. 10 is a graph of classification relation for test results based on $\Delta\omega_{oo}$ and Vh according to an embodiment of the present disclosure.

In the present embodiment, a radial freezing test and a one-dimensional soil column freezing test were respectively performed for each kind of soil samples, the comparison of $\Delta\omega_{oO}$ and the maximum frost heave ratio $V_k$ is shown in FIG. 10, and it is discovered that the two were linearly correlated, which confirmed that the use of $\Delta\omega_{oO}$ for determining the frost susceptibility of soil mass is a reliable and effective method. Using the 8-hour frost heave ratio classification method proposed by the American Society for Testing and Materials (ASTM), the frost susceptibility of soil mass is divided into very high, high, moderate, low, very low, and weak according to $V_k$.

Figure 11:
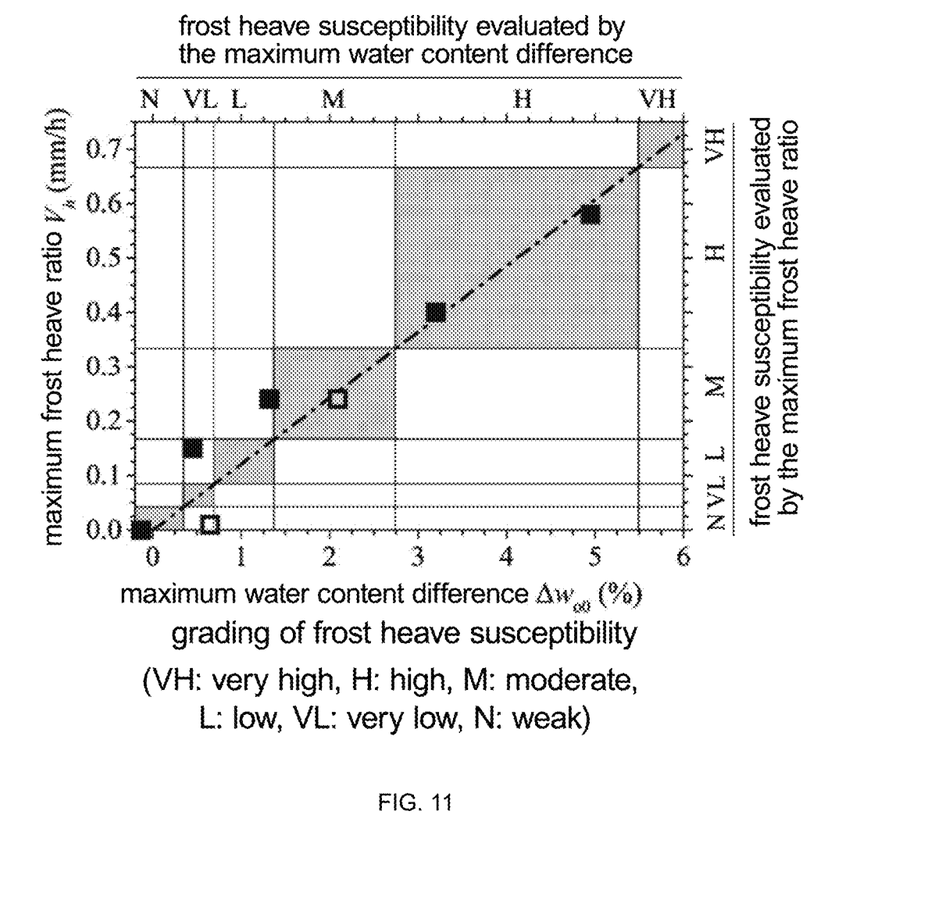
FIG. 11 is a comparison diagram showing classification results for test results based on $\Delta\omega_{oo}$ and Vh according to an embodiment of the present disclosure.

This classification standard is applied to the classification of $\Delta\omega_{oO}$. Through comparison of a large amount of data, $\Delta\omega_{oO}$ is divided in the present embodiment into six ranges, namely 0-0.345%, 0.345%-0.690%, 0.690%-1.379%, 1.379%-2.759%, 2.759%-5.517%, and 5.517% and higher, which respectively indicate that the frost susceptibility of soil mass is weak, very low, low, moderate, high, and very high, as shown in the following table.

regarding the classification results of soil masses insusceptible to frost heave, as shown in FIG. 11, wherein the gray area indicates consistent classification results, while the white area indicates the presence of differences. For example, in clays with a relatively low initial moisture ratio, according to the $V_k$ criterion and the $\Delta\omega_{oO}$ criterion, the frost heave susceptibilities thereof were respectively low and very low. In saline clays, according to the $V_k$ criterion and the $\Delta\omega_{oO}$ criterion, the frost heave susceptibilities thereof were respectively weak and very low. The divergence between the water inhomogeneity classification standard and the frost heave rate classification standard mainly occurs in soil masses with low frost susceptibility.

Although there are some divergences, the final qualitative results of soil masses are not greatly deviated from each other. This limitation could also be overcome with more laboratory tests and field monitoring, hereby allowing more accurate classification methods to be developed.

In general, the present disclosure provides a method for testing frost susceptibility of soils, a soil frost susceptibility instrument, and an electronic apparatus, which can be applied to cold region engineering, can be used in engineering sites, can acquire the frost susceptibility of soil masses conveniently, efficiently and quickly, can meet requirements of projects on economic costs, time, and accuracy to a certain extent, and can also provide convenience for applications such as study and design for roadbed and foundation and soil stability measurement. It can also be used to simulate changes of moisture content of frost heaved soil mass in the region where a project is located, so as to determine the frost susceptibility of the soil mass accordingly. In engineering field tests, it is much quicker and more convenient to measure changes of moisture content than to test the frost heave amount. Thus, the frost susceptibility of soil mass is determined by measuring changes in moisture ratio of a soil sample or moisture ratio distribution, and the time for measuring the frost susceptibility of soil mass can be greatly shortened while ensuring the accuracy of the results. As for the one-dimensional soil column freezing test according to the prior art, each device can only accommodate one specimen at a time; while multiple groups of specimen tests can be performed at a time in the freezing test according to the present disclosure, wherein the success rate and the accuracy of the test are improved indirectly. The one-dimensional soil column freezing test according to the prior art is temperature sensitive, and the temperature influ-

|  | $\Delta\omega_{oO}$ | | | | | |
|---|---|---|---|---|---|---|
|  | 0-0.345% | 0.345%-0.690% | 0.690%-1.379% | 1.379%-2.759% | 2.759%-5.517% | 5.517% and higher |
| Frost susceptibility of soil samples | Weak | Very low | Low | Moderate | High | Very high |

Through multiple groups of experiments, specimens were classified according to the frost susceptibility respectively depending on $V_k$ and $\Delta\omega_{oO}$, and it is found that the susceptibility of soil mass to water migration was highly correlated with the frost susceptibility. According to the frost heave ratio classification method proposed by the American Society for Testing and Materials (ASTM), soil samples were classified based on $\Delta\omega_{oO}$, and the results were almost identical. Thus, the technical solution of the present disclosure is reliable. There is a minor divergence only in the test results ences test results; while the present disclosure is not sensitive to temperature, and the accuracy and the convenience of the test are improved.

The embodiments of device and system described above are merely schematic, and partial or all modules therein may be selected according to actual requirements to achieve the purpose of the solution of the present embodiment. A person ordinarily skilled in the art could understand and make implementations without creative efforts.

The above mentioned are merely preferred specific embodiments of the present disclosure; however, the scope of protection of the present disclosure is not limited thereto, and any technician familiar with this technical field can readily think of variations or substitutions within the technical scope disclosed in the present disclosure, and these variations and substitutions shall be covered in the scope of protection of the present disclosure. Thus, the scope of protection of the present disclosure shall be defined according to the scope of protection of the claims.

The invention claimed is:

1. A method for testing frost susceptibility of soils, comprising steps of:
    taking a part of a soil sample to be tested as a test soil sample and freezing the test soil sample;
    taking a soil sample of outer layer from the test soil sample after completion of the freezing and measuring a moisture ratio of the soil sample of outer layer; and
    determining a frost susceptibility of the soil sample to be tested based on an initial moisture ratio and the moisture ratio of the soil sample of outer layer or based on the moisture ratio of the soil sample of outer layer and a moisture ratio of a soil sample of inner layer from the test soil sample after completion of the freezing,
    wherein the moisture ratio of the soil sample of inner layer from the test soil sample after completion of the freezing is obtained by taking the soil sample of inner layer from the test soil sample after completion of the freezing and then measuring the moisture ratio of the soil sample of inner layer.

2. The method according to claim 1, wherein
    the step of determining a frost susceptibility of the soil sample to be tested based on an initial moisture ratio and the moisture ratio of the soil sample of outer layer comprises: determining a level of the frost susceptibility of the soil sample to be tested according to a variation value in moisture ratio obtained by subtraction between the moisture ratio of the soil sample of outer layer and the initial moisture ratio and in accordance with a set range, in which the variation value in moisture ratio falls; and
    the step of determining a frost susceptibility of the soil sample to be tested based on the moisture ratio of the soil sample of outer layer and a moisture ratio of a soil sample of inner layer from the test soil sample after completion of the freezing comprises: determining a level of the frost susceptibility of the soil sample to be tested according to a moisture ratio difference obtained by subtraction between the moisture ratio of the soil sample of outer layer and the moisture ratio of the soil sample of inner layer from the test soil sample after completion of the freezing and in accordance with a set range, in which the moisture ratio difference falls.

3. The method according to claim 2, wherein the step of freezing the test soil sample comprises:
    performing a heat insulating treatment on upper and lower surfaces of the test soil sample with a heat insulating material; and
    placing the test soil sample after the heat insulating treatment into a freezer for freezing.

4. The method according to claim 2, wherein the test soil sample is a columnar soil sample excised by a cutting ring; and the step of taking a soil sample of outer layer from the test soil sample after completion of the freezing comprises: obtaining the soil sample of outer layer by cutting an outer layer of the test soil sample using the cutting ring.

5. The method according to claim 2, wherein the moisture ratio is measured through steps of:
    measuring a mass of moisture loss of a soil sample by drying as a moisture content; and
    obtaining the moisture ratio according to a total mass of the soil sample and a measured moisture content.

6. The method according to claim 1, wherein the method further comprises a step of obtaining the initial moisture ratio, the step comprising:
    taking a part of the soil sample to be tested as initially measured soil sample; and
    measuring a moisture ratio of the initially measured soil sample as the initial moisture ratio.

7. The method according to claim 6, wherein the step of freezing the test soil sample comprises:
    performing a heat insulating treatment on upper and lower surfaces of the test soil sample with a heat insulating material; and
    placing the test soil sample after the heat insulating treatment into a freezer for freezing.

8. The method according to claim 6, wherein the test soil sample is a columnar soil sample excised by a cutting ring; and the step of taking a soil sample of outer layer from the test soil sample after completion of the freezing comprises: obtaining the soil sample of outer layer by cutting an outer layer of the test soil sample using the cutting ring.

9. The method according to claim 6, wherein the moisture ratio is measured through steps of:
    measuring a mass of moisture loss of a soil sample by drying as a moisture content; and
    obtaining the moisture ratio according to a total mass of the soil sample and a measured moisture content.

10. The method according to claim 1, wherein the method further comprises a step of obtaining the initial moisture ratio, the step comprising:
    using a remaining part after removal of the soil sample of outer layer from the test soil sample after completion of the freezing as remaining soil sample;
    measuring a moisture content of the remaining soil sample;
    obtaining a total moisture content by adding a moisture content of the soil sample of outer layer and the moisture content of the remaining soil sample together; and
    obtaining a total moisture ratio as the initial moisture ratio by dividing the total moisture content by a total mass of the test soil sample before the freezing or after completion of the freezing.

11. The method according to claim 10, wherein the step of freezing the test soil sample comprises:
    performing a heat insulating treatment on upper and lower surfaces of the test soil sample with a heat insulating material; and
    placing the test soil sample after the heat insulating treatment into a freezer for freezing.

12. The method according to claim 10, wherein the test soil sample is a columnar soil sample excised by a cutting ring; and the step of taking a soil sample of outer layer from the test soil sample after completion of the freezing comprises: obtaining the soil sample of outer layer by cutting an outer layer of the test soil sample using the cutting ring.

13. The method according to claim 10, wherein the moisture ratio is measured through steps of:
    measuring a mass of moisture loss of a soil sample by drying as a moisture content; and
    obtaining the moisture ratio according to a total mass of the soil sample and a measured moisture content.

14. The method according to claim 1, wherein the step of freezing the test soil sample comprises:
performing a heat insulating treatment on upper and lower surfaces of the test soil sample with a heat insulating material; and
placing the test soil sample after the heat insulating treatment into a freezer for freezing.

15. The method according to claim 1, wherein the test soil sample is a columnar soil sample excised by a cutting ring; and the step of taking a soil sample of outer layer from the test soil sample after completion of the freezing comprises: obtaining the soil sample of outer layer by cutting an outer layer of the test soil sample using the cutting ring.

16. The method according to claim 1, wherein the moisture ratio is measured through steps of:
measuring a mass of moisture loss of a soil sample by drying as a moisture content; and
obtaining the moisture ratio according to a total mass of the soil sample and a measured moisture content.

17. An instrument for testing frost susceptibility of soils, wherein the instrument for testing frost susceptibility of soils is applicable to performing a freezing test on the test soil sample according to claim 1, and the instrument for testing frost susceptibility of soils comprises:
a box body;
a first cutting ring and a second cutting ring, wherein a diameter of the first cutting ring is greater than a diameter of the second cutting ring,
wherein the first cutting ring is configured to accommodate the test soil sample; and the second cutting ring is configured to excise a part of a radial periphery of the test soil sample as the soil sample of outer layer;
a freezer, which is fixed in the box body and configured to freeze the test soil sample, wherein the freezer comprises a connecting structure detachable from the first cutting ring;
a heater, which is provided in the box body and configured to dry and remove moisture from the soil sample so as to measure a moisture content; and
an electronic scale, which is provided in the box body and configured to weigh the soil sample.

* * * * *